(12) United States Patent
Aguirre et al.

(10) Patent No.: US 8,628,548 B2
(45) Date of Patent: Jan. 14, 2014

(54) DELIVERY SYSTEM FOR MAGNETIC ANASTOMOSIS DEVICE

(75) Inventors: Andres F. Aguirre, Burlington, NC (US); Brian K. Rucker, King, NC (US); Kevin Chmura, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 680 days.

(21) Appl. No.: 12/753,583

(22) Filed: Apr. 2, 2010

(65) Prior Publication Data
US 2010/0256659 A1 Oct. 7, 2010

Related U.S. Application Data

(60) Provisional application No. 61/166,453, filed on Apr. 3, 2009.

(51) Int. Cl.
*A61B 17/08* (2006.01)
(52) U.S. Cl.
USPC ......................................... 606/153
(58) Field of Classification Search
USPC ................. 606/10, 153, 151; 623/23.64
See application file for complete search history.

(56) References Cited

U.S. PATENT DOCUMENTS

| | | | |
|---|---|---|---|
| 5,690,656 A * | 11/1997 | Cope et al. | 606/153 |
| 6,273,917 B1 | 8/2001 | Inoue | |
| 6,802,847 B1 | 10/2004 | Carson et al. | |
| 6,932,827 B2 | 8/2005 | Cole | |
| 2004/0107004 A1 | 6/2004 | Levine et al. | |
| 2005/0070821 A1 * | 3/2005 | Deal et al. | 600/585 |
| 2005/0080439 A1 | 4/2005 | Carson et al. | |
| 2005/0228412 A1 * | 10/2005 | Surti | 606/153 |
| 2008/0114384 A1 | 5/2008 | Chang et al. | |
| 2009/0125042 A1 | 5/2009 | Mouw | |
| 2012/0035628 A1 | 2/2012 | Aguirre et al. | |

FOREIGN PATENT DOCUMENTS

WO WO 2008/061024 A2 5/2008
WO WO 2010/115116 A1 10/2010

OTHER PUBLICATIONS

International Search Report and Written Opinion (PCT/US10/029801), dated Jun. 16, 2010.
International IPRP (PCT/US10/029801), dated Oct. 13, 2011.
International Search Report/Written Opinion for PCT/US2010/061083 dated Apr. 21, 2011.
IPRP for PCT/US2010/061083 dated Jul. 4, 2012.

* cited by examiner

*Primary Examiner* — Thomas McEvoy
*Assistant Examiner* — Tin Nguyen
(74) *Attorney, Agent, or Firm* — Brinks Gilson & Lione

(57) ABSTRACT

A magnet delivery system for forming an anastomosis that comprises a wire guide; a catheter having a delivery portion for advancement into a jejunal space, the delivery portion having a lumen extending at least partially therethrough, a first port and a second port through which the wire guide is disposed; a magnet comprising a lumen therethrough wherein the magnet is removably secured to the delivery portion of the catheter between the first and second ports by disposing the wire guide through the lumen of the magnet, the first port, and the second port.

13 Claims, 7 Drawing Sheets

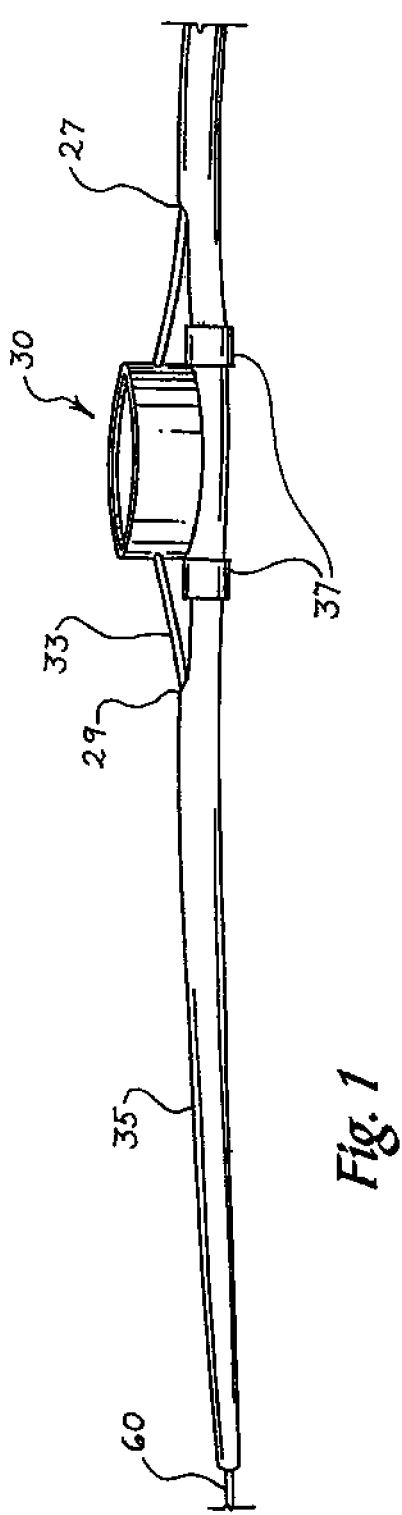
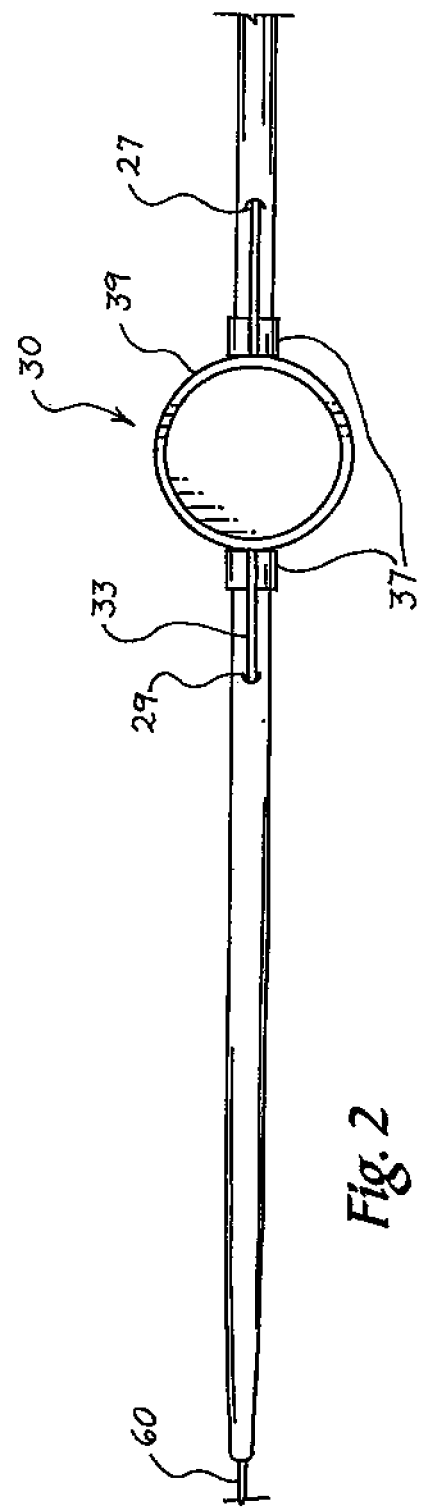

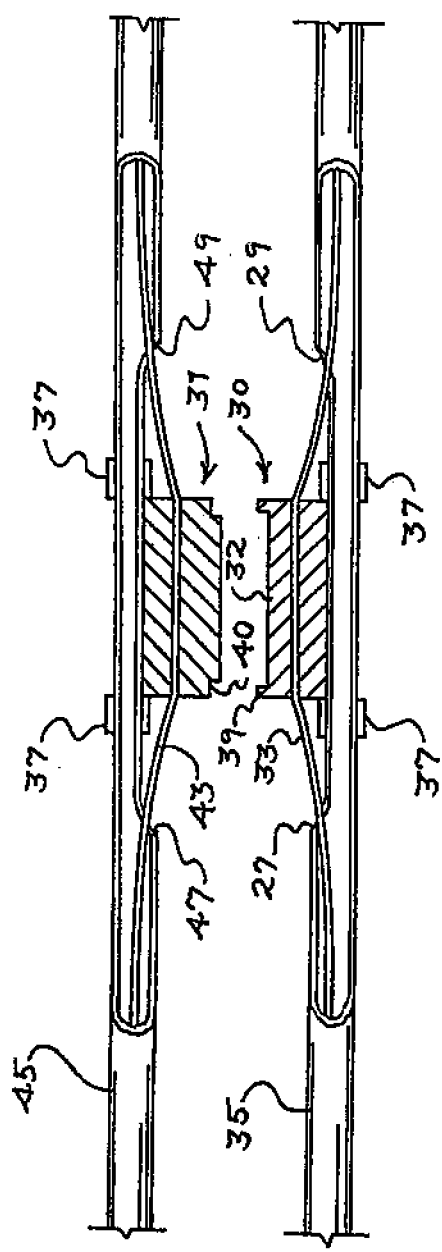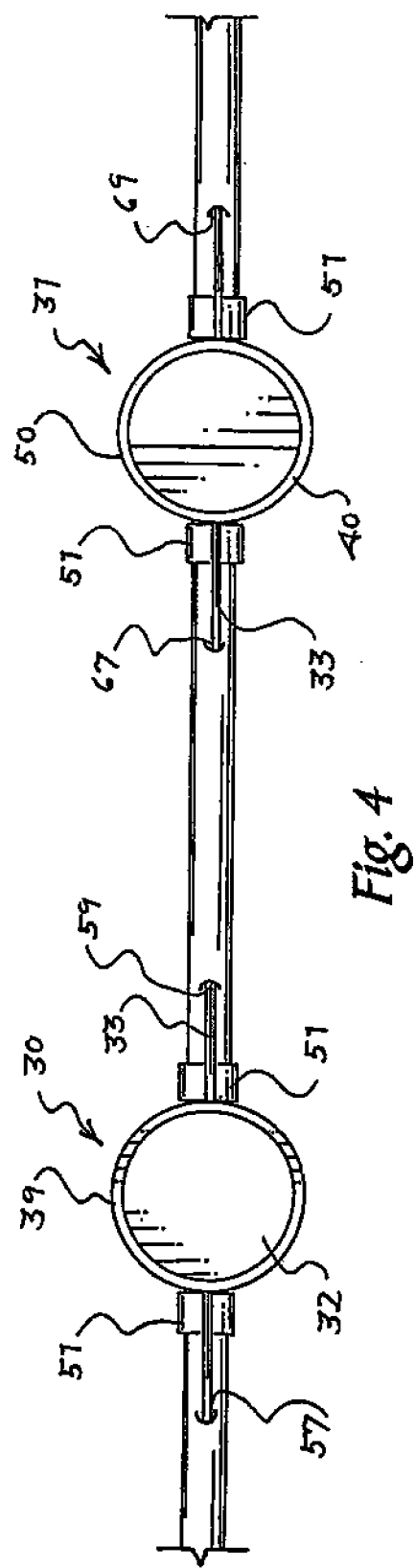

DELIVERY SYSTEM FOR MAGNETIC ANASTOMOSIS DEVICE

CROSS-REFERENCE TO RELATED APPLICATIONS

This application claims the benefit of U.S. Provisional Application Ser. No. 61/166,453 filed on Apr. 3, 2009, entitled "DELIVERY SYSTEM FOR MAGNETIC ANASTOMOSIS DEVICE," the entire contents of which are incorporated herein by reference.

FIELD OF THE INVENTION

The present invention relates to delivery devices useful in delivering magnetic anastomosis devices.

BACKGROUND OF THE INVENTION

Magnetic anastomosis devices (MADS) are currently used to create a channel between two viscera for the purpose of redirecting bodily fluids. For example, intestinal contents or bile may be redirected in patients who have developed an obstruction of the bowel or bile duct due to such conditions as tumor, ulcer, inflammatory strictures, or trauma. A magnetic anastomosis device is disclosed in U.S. Pat. No. 5,690,656, the disclosure of which is incorporated herein by reference in its entirety. Generally, the MAD includes first and second magnet assemblies comprising magnetic cores that are surrounded by thin metal rims. Due to the magnetic attraction between the two magnetic cores, the walls of two adjacent viscera may be sandwiched and compressed between the magnet assemblies, resulting in ischemic necrosis of the walls to produce an anastamosis between the two viscera. The viscera treated by MADS include the gall bladder, the common bile duct, the stomach, the duodenum, and the jejunum of the small intestine.

Historically, MADS have been delivered through surgical intervention such as laparotomy, which of course is invasive and carries its own risks. The exemplary self-centering MAD of U.S. Pat. No. 5,690,656 permits delivery of the device over a wire guide and through the oral cavity, and typically under fluoroscopy. Alternatively, delivery can be accomplished by simply swallowing the magnet assemblies of the MAD and using massage under fluoroscopy to center the two magnet assemblies. Finally, delivery of the magnet assemblies has occasionally been performed endoscopically with grasping forceps, which can be time consuming and difficult. Removal of the MAD is typically accomplished by allowing the magnet assemblies to pass through the gastrointestinal track naturally, or more typically, with a follow-up endoscopic procedure using grasping forceps. Unfortunately, the relatively large size of the magnet assemblies can make delivery and retrieval complicated. In fact, balloon dilation of bodily lumens is often required in order to deliver the magnet assemblies to the desired location. Likewise, the size of bodily lumens is often the limiting factor in the size of the magnet assemblies that can be delivered and deployed.

Certain MAD procedures utilizing a jejunal magnet require the magnet to be passed down the esophagus to the stomach, and then through the pylorus and into the jejunum. Because of the curved nature of the passages leading to the jejunum, the magnet often becomes dislodged from the delivery system during advancement and placement thereof. Passing the jejunal magnet through the pylorus may be further complicated by patients with gastric outlet obstruction.

BRIEF SUMMARY OF THE INVENTION

Herein provided is a magnet delivery system for forming an anastomosis in a visceral space. The delivery system comprises a wire guide, a catheter, and a magnet. The catheter has a delivery portion for advancement into a space. This delivery portion has a lumen extending at least partially therethrough, a first port, and a second port in communication with the lumen and through which the wire guide is disposed. The magnet comprises a lumen through which the wire guide is disposed. The magnet is removably secured to the delivery portion of the catheter between the first and second ports by disposing the wire guide through the lumen of the magnet, the first port, and the second port.

Also provided is a method for delivering a jejunal magnet for forming an anastomosis between two bodily walls. The delivery system provided herein is introduced into a bodily organ, such as any of the viscera. The magnet, which is on the delivery portion of the catheter, is positioned adjacent the wall of a first organ. To deliver the magnet, the wire guide is withdrawn from the lumen of the magnet.

Also provided is a system having a delivery portion further comprising an additional first port, an additional second port, and an additional magnet that also comprises a lumen therethrough. The additional magnet is located between the additional first and second ports. The wire guide is placed through the lumen of the additional magnet such that it can be withdrawn later to deliver the magnet. There can be a single wire or separate wires. Such systems may allow the delivery of multiple magnets during a minimum number of procedures.

The delivery system can be used in tandem with a second magnet delivery system as previously described. This second magnet delivery system may be used to position a second magnet adjacent the wall of a second organ such that it will be attracted to the first magnet placed adjacent to the wall of the first organ.

As described herein, the magnet is firmly attached to the delivery catheter and the likelihood of the magnet becoming dislodged during the procedure is minimized. The system described herein makes it possible to push the magnet through a gastric outlet obstruction.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 1 is a perspective view of the delivery system described herein;

FIG. 2 is an overhead view of the delivery system;

FIG. 3 is a perspective view of two delivery systems with complementary jejunal magnets;

FIG. 4 is an overhead view of a dual delivery system;

DETAILED DESCRIPTION OF THE INVENTION

Figure 5:
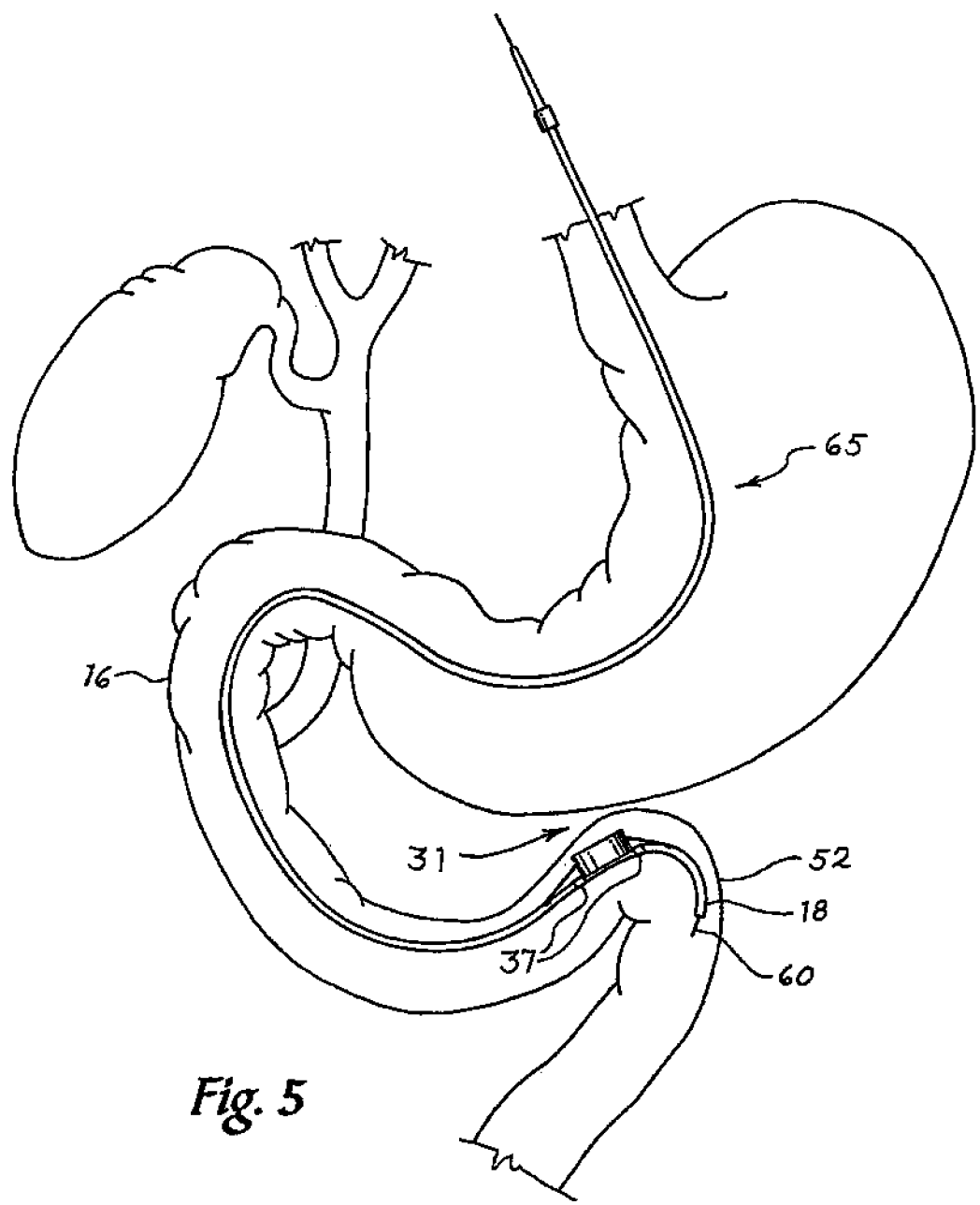
FIGS. 5, 6, and 7 schematically depict the use of two magnet assemblies for forming a magnetic anastamosis device in accordance with the present description.

The term "prosthesis" means any replacement for a body part or for a function of that body part or any device that enhances or adds functionality to a physiological system. The terms "proximal" and "distal" as used herein are intended to have a reference point relative to the user. Specifically, throughout the specification, the terms "distal" and "distally" shall denote a position, direction, or orientation that is generally away from the user and towards a target site, and the terms "proximal" and "proximally" shall denote a position, direction, or orientation that is generally towards the user and away from a target site. Thus, "proximal" and "distal" directions, portions of a device, or bodily regions, may depend on the point of entry for the procedure (e.g., percutaneously or laparoscopically or endoscopically).

The term "catheter" generally means a medical device comprising an elongate shaft having a lumen extending at least partially therethrough, including balloon catheters, guide catheters, and delivery catheters. An example of a catheter includes the Cook Medical Fusion™ Biliary Dilation Catheter (FS-BDC).

The magnet delivery system uses a catheter 35 and a wire guide 33 to deliver a jejunal magnet 30. As seen in FIG. 1, the catheter 35 has two ports, a first port 27 and a second port 29 in communication with the lumen of the catheter and through which the wire guide 33 is placed. Suitable wire guides can include the Cook Medical Tracer Hybrid® Wire Guides (HYB-48015). The proximal 27 and distal 29 ports are sufficiently spaced apart to accommodate the magnet 30 between them. The ports 27, 29 are about 35 mm to about 70 mm apart or any combination or subcombination of ranges therein. In the particular embodiment illustrated, the ports 27, 29 can be spaced about 60 mm apart. The first and second ports 27, 29 are formed through the catheter 35 wall and are spaced proximally from the distal end of the catheter 35 so as to be distinguished from the entry or exit openings of the catheter at the very proximal or distal ends thereof. The ports 27, 29 are preferably longitudinally aligned. The preferred distance between the ports will depend on the diameter and size of the magnets. Magnet sizes will range across standard sizes used in the field. These ports 27, 29 are located in the distal part of the catheter 35 and are appropriately spaced to accommodate magnets of various sizes in diameter. Magnets between about 10 mm and 20 mm in diameter or any combination or subcombination of ranges therein may be accommodated, although a magnet about 14 mm in diameter is illustrated. For other magnet sizes the location of the ports in the wire guide lumen may be modified as required.

The magnet 30 shown has a general disc shape (i.e. having an axial height which is less than the outer diameter). Magnets that may be used in this delivery system can be circular, cubular, cyclindrical, polygonal, oval or ovoid, square, or the like. Numerous other shapes of the magnets may be readily envisioned by those skilled in the art. For example, referring to FIGS. 8a, 8b and 9, the magnet may include an elongate magnet as described in U.S. Provisional Application No. 61/291,202, entitled "Elongate Magnet for a Magnetic Anastomosis Device," the entire contents of which are incorporated herein by reference. The magnet 30 may include a protective coating which may be formed of various materials such as polymers like Teflon® or Paralene® for protection of the magnetic core from the corrosive effects of digestive acids or other bodily fluids depending upon the bodily structure involved.

The magnet 30 has a lumen therethrough to accommodate the wire guide 33. The magnet 30 also comprises an annular edge 39 along the magnet's perimeter. The edge 39 is slightly raised above the center of the magnet 30 such that it forms a basin 32 to accommodate or mate with a second magnet (as described below). In particular, when the magnet 30 is delivered, this edge 39 contacts the wall of the viscera and helps to initiate the ischemic necrosis of the tissue captured between the magnet 30 and a mated second magnet. A radiopaque marker 37 is placed on the catheter in the vicinity of the magnet to mark the magnet location when viewed through fluoroscopy. A radiopaque marker can be placed underneath the magnet 30 on the catheter 35 to mark the location of the magnet when viewing the delivery system from the side.

The wire guide 33 holds the magnet 30 in place on the distal end of the catheter 35. In FIGS. 1 and 2, the wire guide 33 is shown protruding from the first port 27, going through the lumen of the magnet 30, and re-entering the catheter 35 at the second port 29. The catheter 35 may include radiopaque markers 37 that permit tracking of the delivery system for accurate positioning of the magnet 30. It may be preferred that a radiopaque marker 37 be placed immediately distal to the magnet 30. The catheter 35 may be used alone or in conjunction with other wire guide cannulae for navigation of the bodily lumens and delivery of a magnet.

Figure 7:
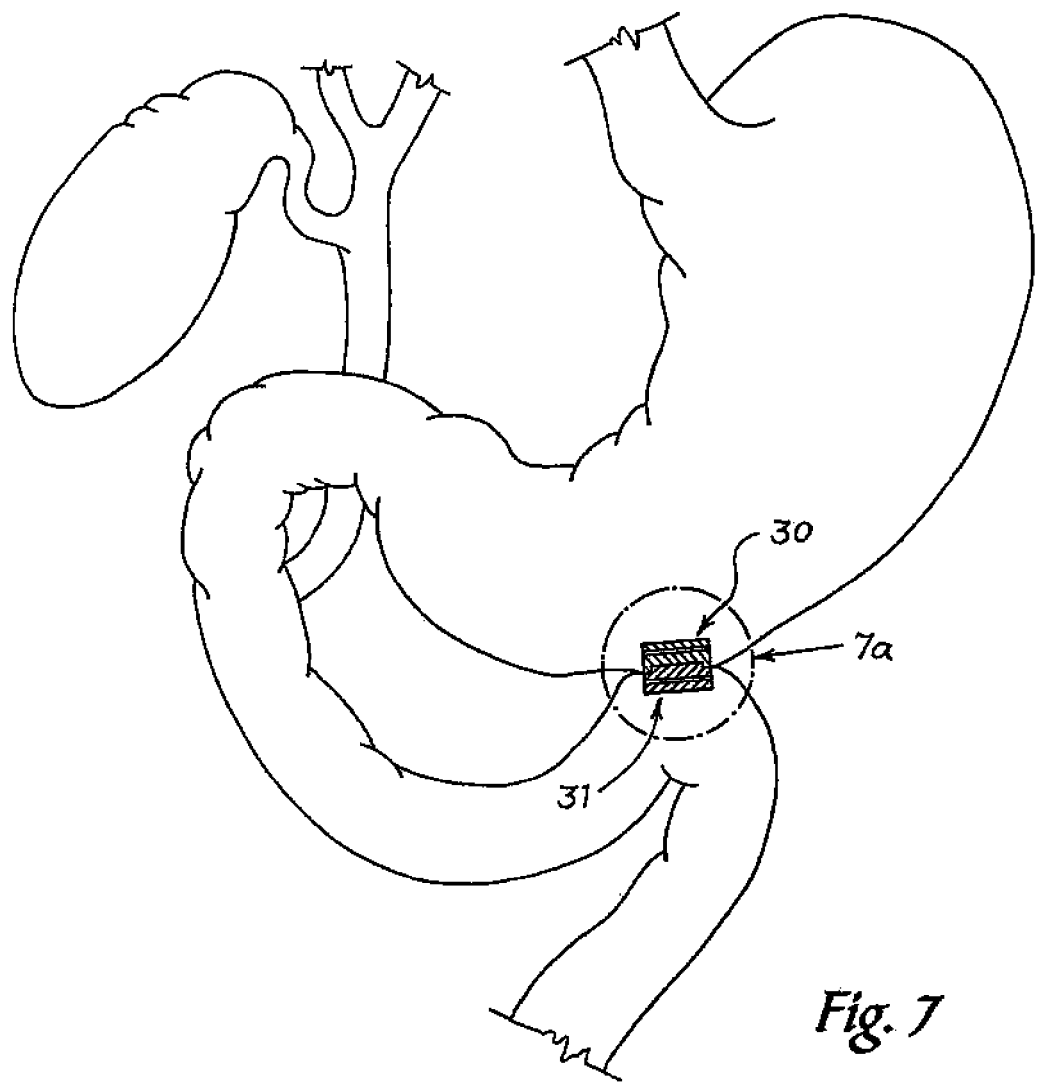
Figure 7A:
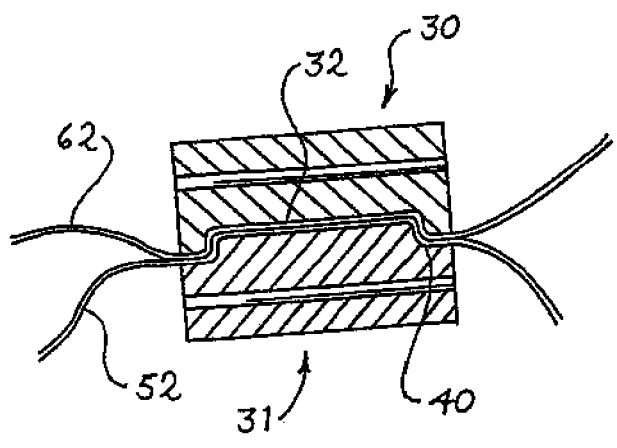
FIG. 7a is a cross-sectional view of two magnets compressing the walls of two internal bodily organs to facilitate a new anastamosis.

FIG. 3 shows two delivery systems where a second magnet 31 is affixed to a second catheter 45 using second wire guide 43 protruding from first port 47 and re-entering catheter 45 at the second port 49. The second magnet 31 has an annular recess 40 that is capable of mating with the annular edge 39 of the first magnet 30. FIG. 7a shows the walls 52, 62 of two viscera being compressed between magnets 30, 31. The edge 39 compresses the walls against the second magnet 31 to assist the ischemic necrosis. The second magnet 31 can also have an annular edge with a smaller diameter than the first magnet 30. When implanted and mated with the first magnet 30, the second magnet 31 can fit within the annular edge 39 of the first magnet 30.

FIG. 4 shows a system for the delivery of two magnets 30, 31. Such a system may be used as an efficient means of delivering multiple magnets. Although two magnets 30, 31 are shown, more than two magnets can be coupled to a catheter in the fashion described herein. The catheter has four holes in total: first 57 and second 67 proximal ports and first 59 and second 69 distal ports. First magnet 30 is held between first port 57 and second port 59 with wire guide 33. The second magnet 31 is constrained between first port 67 and second port 69 with wire guide 33. The first magnet 30 comprises an annular edge 39 with a basin 32. The annular recess 40 on the second magnet 31 mates with the annular edge 39 of the first magnet 30 when both magnets 30, 31 are implanted. Two sets of radiopaque markers 51 can be used with a second radiopaque marker located distal to the second magnet 31. In general, the radiopaque markers can be located on the delivery portion sufficient to guide an operator during the placement procedure. Methods for delivering both magnets using such a system are described further below.

It will be recognized by those skilled in the art that the magnetic anastamosis device employing the magnet assemblies described herein not only preserves the benefits of improving the time of the procedure to place the magnet, but further provides a small delivery configuration which may be easily located within the body for accurate delivery. The delivery systems described herein also provide for insertion of the magnets through natural orifices. As such, there is also a method for delivering the magnet assembly to a position for forming an anastamosis between two viscera. FIG. 5 shows the relative positions of several viscera in the abdominal cavity, including the gall bladder 10, the common bile duct 12, the stomach 14, the duodenum 16, and the jejunum 18 of the small intestine. Although not shown, the delivery system described herein may also be used to implant anastomosis-forming magnets in the colon for possible use in gastric bypass procedures. The delivery system described herein can be used, for example, to create an anastomosis between the stomach 14 and the jejunum 18 of the small intestine. The delivery system can also be used as a part of procedure where forceps are used to place one of the magnets.

The method for delivering a jejunal magnet to form an anastomosis comprises introducing the delivery system 65 into an endoluminal vessel. FIG. 5 shows the system 65 being advanced to the jejunum 18. The delivery of magnet 31 follows once the wire guide 60 has been positioned adjacent the wall of a first viscus. In FIG. 5, the first viscus is the jejunum 18. The magnet 31 is placed on catheter 35 as shown in FIG. 1 and held in place on the catheter 35 by the wire guide 33. The wire guide 33 is loaded through the catheter 35, passing through second port 29 in the catheter 35 lumen, through the lumen of the magnet 30, and then reentering the catheter 35 lumen through first port 27. Using the radiopaque markers 37 as a guide, the catheter 35 is advanced such that the magnet 31 is placed adjacent to the wall of the jejunum 18 as shown in FIG. 6.

Figure 6:
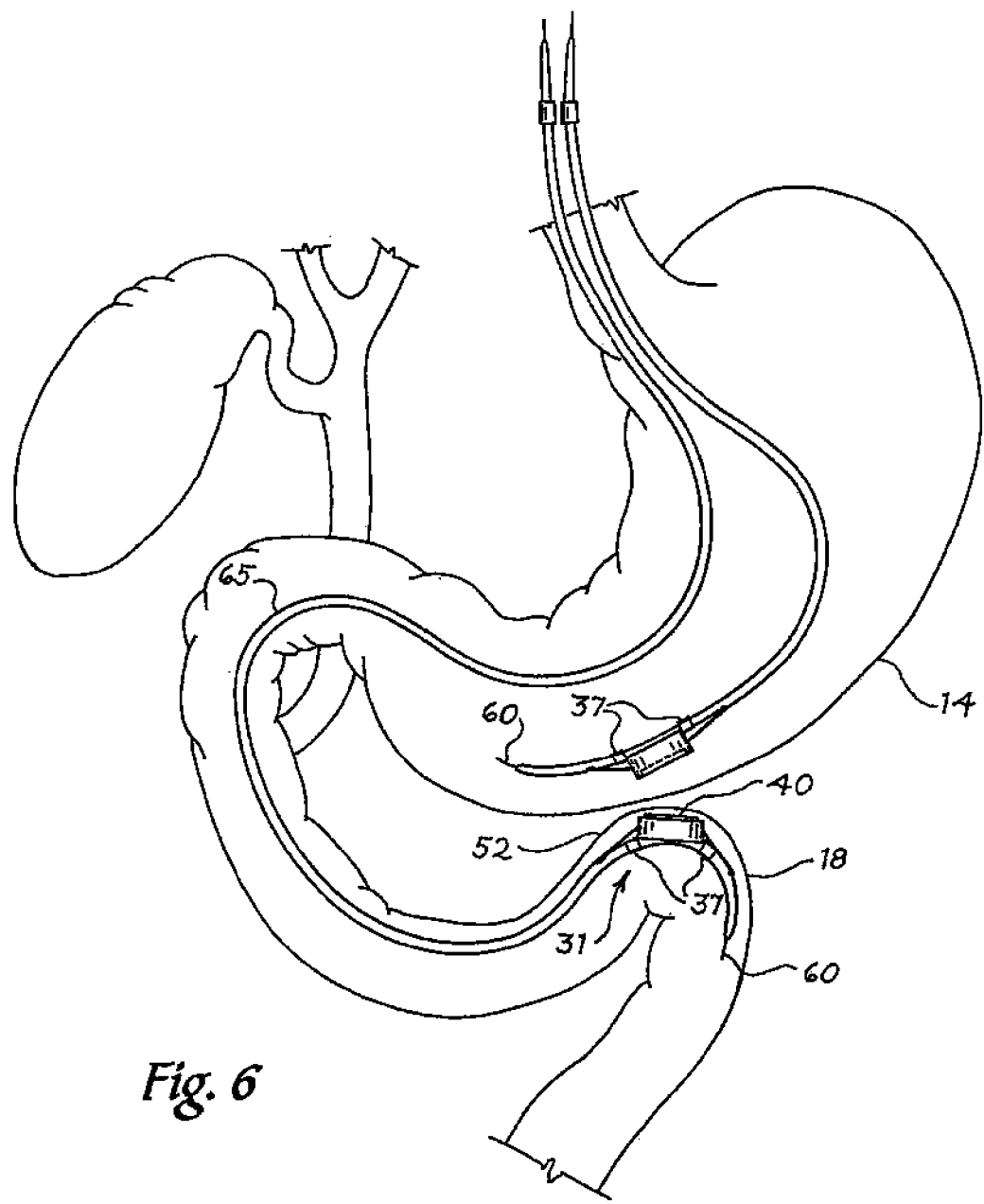

The delivery system 65 with magnet 31 remains in position as a second delivery system 70 is introduced into the stomach 14 as shown in FIG. 6. Magnet 30 is positioned adjacent the wall of the stomach 14 that borders the jejunum 18 near the location of magnet 31. Magnets 30, 31 are released so that the magnetic forces attract the magnets together, compressing the walls 52, 62 together of the jejunum 18 and the stomach 14 as seen in FIG. 7. To release magnet 31, the operator removes the wire guide 33 and then the catheter 35.

The attraction forces exerted between the magnets 30, 31 is strong enough so that in the event that the catheter 35 is caught between the two magnets 30, 31 after the placement of magnet 30, the catheter 35 may be removed and the magnets 30, 31 will remain together. The radiopaque markers 37 can be used as a guide to help position the magnet 31 in the correct orientation under fluoroscopy. A radiopaque marker 37 may be located at the proximal edge of the magnet as exemplified in FIG. 1.

Once the necrosis of the walls of the stomach and the jejunum is complete, an anastomosis is formed. The magnets 30, 31 can then pass through the body naturally or can be removed by means such as laparotic removal, endoscopic removal, or other procedure.

The delivery system shown in FIG. 4 can be used to deliver two magnets using one catheter. Magnet 31 can be delivered first to a first location to be treated by retracting the guidewire 33 sufficiently to release the magnet 31. The delivery portion of the catheter can then be positioned in a second location where magnet 30 can be released by further retracting the guidewire 33 from the lumen of the magnet 30. The magnets 30, 31 can be maneuvered to mate with one another by massage under fluoroscopy or by grasping forceps through laparoscopic surgery. Once mated, the ischemic necrosis process can begin on the walls of the two viscera being treated.

Figure 8A:
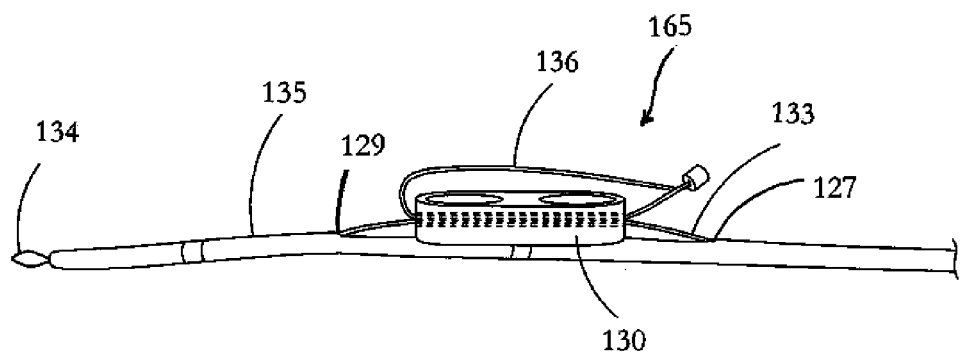
FIGS. 8a and 8b are perspective views of a delivery system for delivering a magnetic anastomosis device constructed in accordance with further teachings of the present description.
Figure 8B:
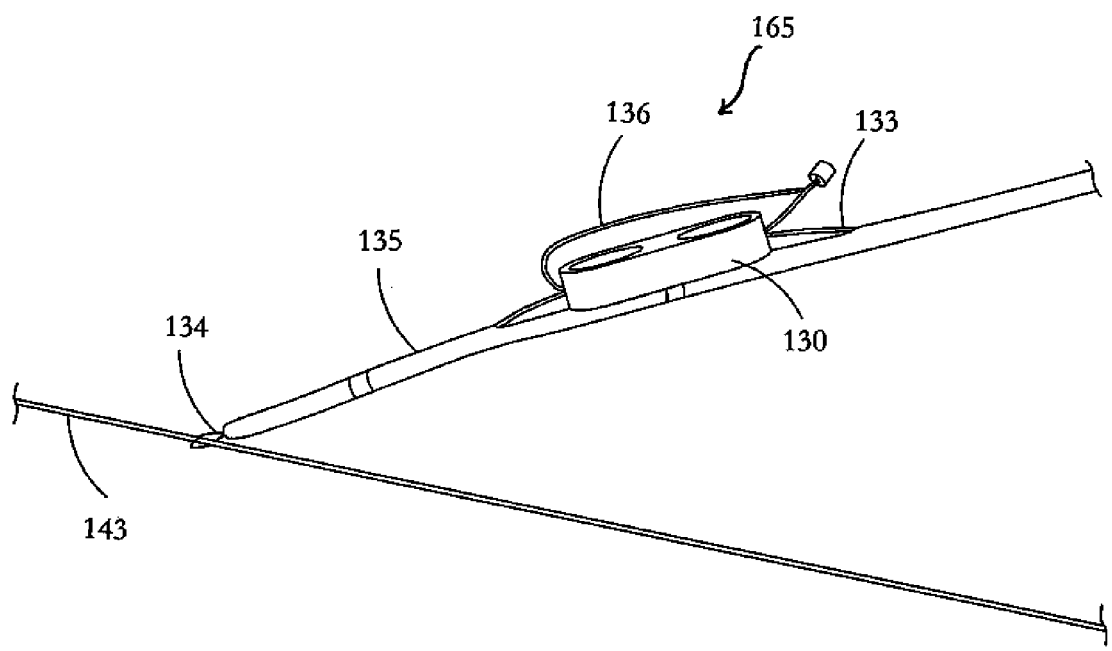

FIGS. 8a and 8b depict an alternative embodiment of a delivery system 165 in accordance with the teachings of the present description and having a description similar to that of FIG. 1, and in which similar components are denoted by similar reference numerals increased by 100. The delivery system 165 uses a catheter 135 with ports 127 and 129 and a wire guide 133 to deliver a magnet 130. In this embodiment, the wire guide 133 includes a loop 134 at a distal end thereof. The loop 134 extends beyond a distal end of the catheter 135.

As shown in FIG. 8b, the loop 134 slides over a second wire guide 143 during delivery of the magnet 130. For example, in one method of delivery, the wire guide 143 is positioned in the target site. The catheter 135 is then backloaded onto the wire guide 143 via the loop 134. In other words, the loop 134 slidably receives the wire guide 143 and the catheter 135 is pushed relative thereto until the target site is reached. The magnet 130 is then placed adjacent a bodily wall. Another magnet is delivered in the same fashion to another target site to mate with the magnet 130 to compress the bodily walls therebetween. Once the magnets mate, the wire guide 143 is removed followed by removal of the wire guide 133. Thereafter, the catheter 135 is removed.

In this embodiment, an elongate magnet 130, as described in U.S. Provisional Application No. 61/291,202, is shown. The elongate magnet 130 may or may not include the suture 136 shown extending through the lumen of the magnet 130 which may aid in positioning of the magnet 130. The delivery system 165 is advantageous for delivering larger, elongate magnets 130. The delivery systems described above may be used to deliver the elongate magnet 130. However, since the elongate magnet 130 is larger than the magnets 30, 31 disclosed in the earlier described embodiments, a greater force would be needed to advance the elongate magnet 130 over the wire guide 33 due to the larger area of friction between the elongate magnet 130 and the catheter 35. With the embodiment shown in FIGS. 8a and 8b, the extra force is eliminated as the magnet 130 moves with the catheter 135 as it slides along the external wire guide 143.

Figure 9:
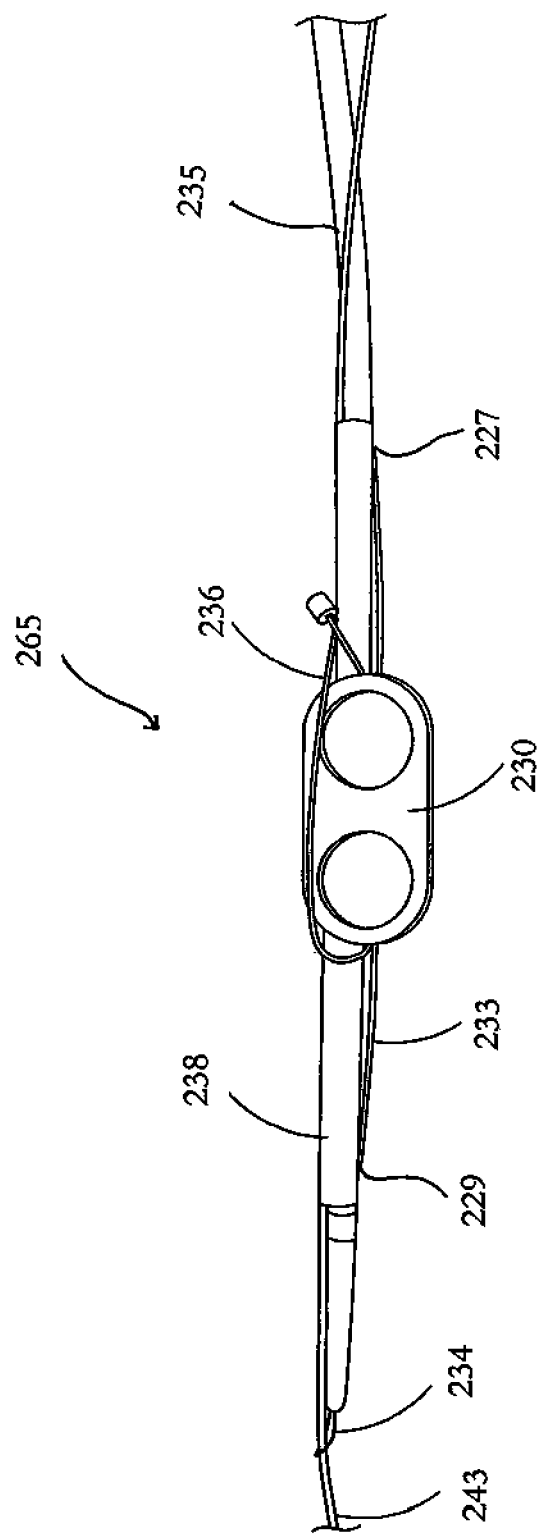
FIG. 9 is an overhead view of a delivery system for delivering a magnetic anastomosis device constructed in accordance with further teachings of the present description.

FIG. 9 depicts another embodiment of a delivery system 265 in accordance with the teachings of the present description and having a description similar to that of FIG. 1, and in which similar components are denoted by similar reference numerals increased by 200. The delivery system 265 uses a catheter 235 and a wire guide 233 to deliver a magnet 230 having suture 236. In this embodiment, the distal loop 234 of the wire guide 233 slidably receives a second wire guide 243, similar to FIGS. 8a and 8b, thus providing reduced force needing during delivery of the magnet 230. In this embodiment, however, a dual lumen outer sheath 238 slidably receives the catheter 235 in one lumen and the wire guide 233 in a second lumen. The outer sheath 238 includes ports 227 and 229.

During delivery of the magnet 230 with the delivery system 265 of FIG. 9, a larger portion of the catheter 235 remains closer to the wire guide 243 rather than merely the distal end as is the case with the system 165 of FIGS. 8a and 8b. This improves the trackability of the catheter 235 and reduces the likelihood that the catheter will bow in the stomach.

Alternatively, instead of being housed within an outer sheath, the catheter 235 may include two lumens; one for the wire guide 233 to hold the magnet and the other for the main wire guide 243. The distal loop 234 slides over the main guide wire 243 during delivery of the magnet 230.

The foregoing description of has been presented for purposes of illustration and description. It is not intended to be exhaustive or to limit the delivery systems and methods disclosed. Numerous modifications or variations are possible in light of the above teachings. The delivery systems and methods disclosed were chosen and described to provide the best illustration of the principles of the delivery systems and methods and their practical application to thereby enable one of ordinary skill in the art to utilize the delivery systems and methods in various embodiments and with various modifications as are suited to the particular use contemplated. All such modifications and variations are within the scope of the delivery systems and methods as determined by the appended claims when interpreted in accordance with the breadth to which they are fairly, legally, and equitably entitled.

The invention claimed is:

1. A magnet delivery system for forming an anastomosis, the delivery system comprising:
   a first wire guide;
   a catheter having a tubular wall and a distal delivery portion for advancement into a visceral space, the delivery portion having a first catheter lumen extending at least partially therethrough, the delivery portion having a first port and a second port formed through the tubular wall and in communication with the first catheter lumen and through which the first wire guide is disposed; and
   a first magnet defining a lumen therethrough, wherein the first magnet is removably secured along an exterior of the delivery portion of the catheter between the first and second ports wherein the first wire guide is disposed through the lumen of the first magnet, the first port and the second port.

2. The magnet delivery system of claim 1 where the first magnet has a disc shape.

3. The magnet delivery system of claim 1 where the first magnet further comprises one of an annular edge and an annular recess.

4. The magnet delivery system of claim 1 where the first magnet includes an elongate jacket enclosing two magnetic members positioned along a longitudinal axis of the elongate jacket.

5. The magnet delivery system of claim 1 where the delivery portion of the catheter further comprises a third port, a fourth port, and a second magnet comprising a lumen therethrough, the second magnet being removably secured to the delivery portion of the catheter between the third and fourth ports, wherein the first wire guide is placed through the lumen of the second magnet, the third port, and the fourth port.

6. The magnet delivery system of claim 5 where the first magnet further comprises an annular edge for placement against the wall of a bodily organ and the second magnet further comprises an annular recess for placement against the wall of a bodily organ.

7. The magnet delivery system of claim 1 further comprising a radiopaque marker located on the delivery portion of the catheter, where the radiopaque marker is proximate the first magnet.

8. The magnet delivery system of claim 1 where the first and second ports are spaced proximally from a distal end of the catheter.

9. The magnet delivery system of claim 1 where the first wire guide includes a loop at a distal end thereof, the delivery system further comprising a second wire guide, wherein the loop of the first wire guide is configured to extend beyond a distal end of the catheter to slidably receive the second wire guide.

10. The magnet delivery system of claim 9 where the catheter includes a second catheter lumen, the first wire guide being disposed within the first catheter lumen and the second wire guide being disposed within the second catheter lumen.

11. The magnet delivery system of claim 9, further comprising an outer sheath having a first sheath lumen and a second sheath lumen, the catheter being disposed within the first sheath lumen and the first wire guide being disposed within the first catheter lumen, and the second wire guide being disposed within the second sheath lumen.

12. The magnet delivery system of claim 1, wherein the first wire guide extends distally through the first catheter lumen at a position distal to the first magnet.

13. The magnet delivery system of claim 1, wherein the first wire guide extends distally through the first catheter lumen, then through the first port, then through the lumen of the first magnet, then through the second port, and again through the first catheter lumen.

* * * * *